(12) United States Patent
Assaly et al.

(10) Patent No.: US 7,348,312 B2
(45) Date of Patent: *Mar. 25, 2008

(54) ALBUMIN-BASED COLLOID COMPOSITION AND METHOD OF USE IN TREATING HYPOVOLEMIA AND MULTIORGAN DYSFUNCTION

(75) Inventors: Ragheb Assaly, Sylvania, OH (US); John D. Dignam, Perrysburg, OH (US); Joseph I. Shapiro, Toledo, OH (US)

(73) Assignee: Medical College of Ohio, Toledo, OH (US)

(*) Notice: Subject to any disclaimer, the term of this patent is extended or adjusted under 35 U.S.C. 154(b) by 19 days.

This patent is subject to a terminal disclaimer.

(21) Appl. No.: 11/387,381

(22) Filed: Mar. 22, 2006

(65) Prior Publication Data

US 2006/0166886 A1   Jul. 27, 2006

Related U.S. Application Data

(63) Continuation of application No. 10/106,793, filed on Mar. 26, 2002, now Pat. No. 7,037,895.

(60) Provisional application No. 60/279,017, filed on Mar. 27, 2001.

(51) Int. Cl.
*A61K 38/38* (2006.01)
(52) U.S. Cl. .............................. 514/12; 530/363; 514/2
(58) Field of Classification Search ................ 530/363; 514/2, 12
See application file for complete search history.

(56) References Cited

U.S. PATENT DOCUMENTS

| | | | |
|---|---|---|---|
| 2,727,027 | A | 12/1955 | Monson et al. |
| 4,101,380 | A | 7/1978 | Rubinstein et al. |
| 4,179,337 | A | 12/1979 | Davis et al. |
| 5,324,844 | A | 6/1994 | Zalipsky |
| 5,583,114 | A | 12/1996 | Barrows et al. |
| 5,650,234 | A | 7/1997 | Dolence et al. |
| 5,704,358 | A | 1/1998 | Zikria |
| 5,714,511 | A | 2/1998 | Saavedra et al. |
| 5,733,563 | A | 3/1998 | Fortier |
| 5,756,481 | A | 5/1998 | Arnal et al. |
| 5,952,009 | A | 9/1999 | Neurath et al. |
| 6,063,764 | A | 5/2000 | Creasey et al. |
| 6,129,912 | A | 10/2000 | Hortin et al. |
| 6,344,197 | B2 | 2/2002 | Fisher et al. |

OTHER PUBLICATIONS

Wu Lin, Martin C. Garnett, Etienne Schacht, Stanley S. Davis, Lisbeth Illum, *Preparation and in vitro characterization of HAS-mPEG nanoparticles*, International Journal of Pharmaceutics, 189 (1999), pp. 161-170.

Angus, D.C., Wax, R.S., *Epidemiology of Sepsis-An Update*, Critical Care Medicine.29(7)(2001) S109-S116.
Baue, A.E. Durham, R. Faist, E., *Systemic Inflammatory Response Syndrome (SIRS) Multiple Organ Dysfunction Syndrome(MODS), Multiple Organ Failure(MOF) Are We Winning The Battle?*, Shock,10(2)(1998) 79-89.
Roberts, J.S., Bratton, S.L., *Colloid volume expanders: problems, pitfalls and possibilities*, Drugs. 55(5)(1998)621-630.
Berger, A., *Why albumin may not work* (editor's commentary). BMJ (1998) 317:240.
Doweiko, J.P., and Nompleggi, D.J., *Interactions of Albumin and Medications*, J. Parenter. Enteral. Nutr. 15,(1991)212-214.
Emerson, T.E., *Unique features of albumin; a brief review*, Crit Care Med. 17(7)(1989)690-694.
Margarson, M.P., Soni. N., *Serum Albumin: touchstone or totem?* Anaesthesia, 53, (1998) 789-803.
McClelland, *Human albumin administration in critically ill patients*, BMJ. 317 (1998)882-886.
Wilkes, M., and Navickis, R.J., *Patient survival after human albumin administration*, Ann Intern Med. 135 (2001)149-164.
Cochrane Injuries Group Albumin Reviewers, *Human albumin administration in critically ill patients: systematic review of randomized controlled trials*, BMJ. 317(1998)235-40.
Delgado, C. Francis, G.E. and Fisher, D., *The uses of properties of PEG-linked proteins*. Critical Reviews in Therapeutic Drug Carrier Systems 9(3,4)(1992)249-304.
Abuchowski, A., van Es, T., Palozuk, N.C., and Davis, F., *Alteration of immunological properties of bovine serum albumin by covalent attachment of polyethylene glycol*, J. Biol Chem. 252(11)(1977)3578-3581.
Kozlowski A; Charles SA; Harris JM, *Development of pegylated interferons for the treatmnet of chronic hepatitis C*, BioDrugs 15 (2001)419-29.
Conover, C., Malatesta, P., Lejuene, Chang, C.L., and Shorr, R.G.L., *The effects of hemodilution with polyethylene glycol bovine hemoglobin(Peg-hb) in a conscious porcine model*, J. Inves Med. 44(5)(1996) 238-246.
Conover, C.D., Lejuene, L, Shum, K., Gilbert, C., and Shorr, R.G., *Physiological effect of polyethyelen glycol conjugation of stroma-free bovine hemoglobin in the conscious dog after partial exchange transfusion*, Artif Organs. 21(5)(1997) 369-78.
Conover, C.D., Linberg, R., Lejuene, L., Nagy, M., and Shum, K.L., *PEG-hemoglobin as a resuscitation solution in the treatment of hypovolemic shock in the anesthetized rat*, Artif. Organs. 23(12)(1999) 1088-1098.
Yeh, T., Parmar, J.M., Rebeyka, I.M., Lofland, G.K., Allen, E.L., Dignan, R.J., et al., *Limiting edema in neonatal cardiopulmonary bypass with narrow-range molecular weight hydroxyethyl starch*, J. Thorac Cardiovasc Surg. 104 (1992)659-65.

(Continued)

Primary Examiner—Maryam Monshipouri
Assistant Examiner—Marsha Tsay
(74) Attorney, Agent, or Firm—Emch, Schaffer, Schaub & Porcello Co., L.P.A.

(57) ABSTRACT

A composition comprising an albumin-based colloid and its use in treating hypovolemic conditions such as capillary leak syndrome and shock are disclosed.

7 Claims, 11 Drawing Sheets
(9 of 11 Drawing Sheet(s) Filed in Color)

OTHER PUBLICATIONS

Axon, R.N., Baird, J.S., Lang, J.D., Brix, A.E., Nielson, V.G., *Pentalyte Decreases Lung Injury After Aortic Occlusion-Reperfusion*, Am J. Reespir.CritCare Med. 157(1998) 1982-1990.

Henekak, M.T., Loschmann, P.A., Osswald, H., *Polymerized Hemoglobin Restores Cadiovascular and Kidney Function in Endotoxin-induced Shock in the Rat*, J.Clin.Invest. 99(1997)47-54.

Zoellner, H., Hoffler, M., Beckmann, R., Hufnagl, Vanyek, E., Blekel E., et al., *Serum albumin is a specific inhibitor of apoptosis in human endothelial cells*, J Cell Science, 109(1996) 2571-2580.

Cantin, A.M., Paquette, B.K. Richter, M., and Larivee, P., *Albumin-mediated regulation of cellular glutathione and nuclear factor Kappa B activation*, Am J Respir Crit Care Med, 162 (2000) 1539-1546.

Assaly, R., Olson, D., Hammersely, J., Fan, P.S., Liu J., Shapiro J., Kahaleh, B., *Initial Evidence of Endothelial Cell Apoptosis as a Mechanism of Systemic Capillary Leak Syndrome*, Chest:120(2001)1301-1308.

Quinlan, G.J., Margarson, M.P., Mumby, S., Evans, T.W., Gutteridge, J.M.C., *Administration of albumin to patients with sepsis syndrome: a possible benefical role in a plasma thiol repletion*, Clin.Sci. 95 (1998) 459-465.

Filep, J.G., Delalandre, A., Beauchamp, M., Dual role for nitric oxide in the regulation of plasma volume and albumin escape during endotoxin shock in conscious rats, Circ. Res., 81 (1997) 840-847.

Tanford, C., *Physical Chemistry of Macromolecules*, John Wiley & Sons, (1961) p. 217.

Vandegriff, K.D., McCarthy, M., Rohlfs, R.J., and Winslow, R.M. *Colloid osmotic properties of modified hemoglobins: chemically cross-linked versus polyethylene glycol surface-conjugated*, Biophys. Chem 69 (1997) 23-30.

Laemmli, U.K., *Cleavage of structural proteins during the assembly of the head of bacteriophage* T4, Nature, 227 (1970) 6980-6985.

Johnson, D.E., *Applied Multivariate Methods for Data Analysis*, Duxbury Press, (1998) p. 319-321.

Bullock, Jr., Characterization of Polyethelene glycol-Modified Superoxide Dismutase: *Comparison of Capillary Electrophoresis and Marix-Assisted Laser Desorption/Ionization Mass Spectometry*, Anal.Chem. 68(1996) 3258-3264.

Veronese, F.M., *Peptide and protein PEGylation: a review of problems and solutions*, Biomaterials 22 (2001)405-417.

Nathan, C., *Inducible Nitric Oxide Synthase: What Difference Does It Make*? J.Clin.Invest., 100(10)(1997) 2417-2423.

Hubbard, J.D., Janssen, H.F., *Increased microvascular permeability for canine endotoxic shock: protective effects of ibuprofen*, Circ Shock 26 (1988) 169-183.

Taylor, AE, Granger DN, Exchange of macromolecules across the microcirculation. Handbook of Physiology, The Cardiovascular System IV, Am Physiol Soc, 4(1)11 (1984)467-520.

Hershey, S.G. and Altura, Burton M.; Effect of Pretreatment with Aggregate Albumin on Reticuloendothelial System Activity and Survival After Experimental Shock; Proceedings of the Society for Experimental Biology and Medicine; Aug.-Sep. 1966—vol. 122, No. 4.

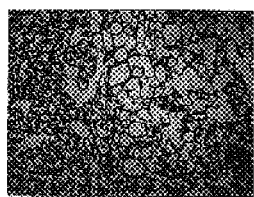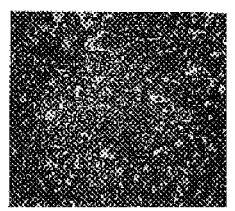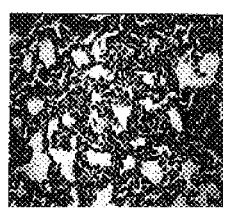
4x　　　40x　　　　　　4x　　　40x
FIG. 3A　　　　　　FIG. 3B
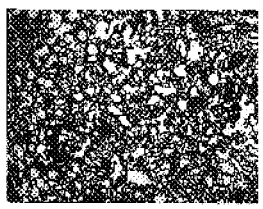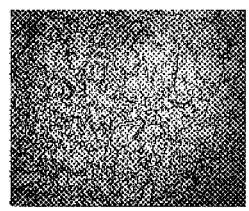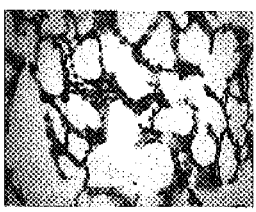
4x　　　40x　　　　　　4x　　　40x
FIG. 3C　　　　　　FIG. 3D

ALBUMIN-BASED COLLOID COMPOSITION AND METHOD OF USE IN TREATING HYPOVOLEMIA AND MULTIORGAN DYSFUNCTION

CROSS REFERENCE TO RELATED APPLICATION

This application is a continuation of and claims the benefit of U.S. patent application Ser. No. 10/106,793 filed Mar. 26, 2002 now U.S. Pat. No. 7,037,895.

This application claims the benefit of U.S. Provisional Application(s) No(s).: 60/279,017 Mar. 27, 2001

Throughout this application various publications are referenced by numerals within parenthesis. Full citations for these publications may be found at the end of this application, preceding the claims. The disclosure of these publications in their entireties are hereby incorporated by reference into this application in order to more fully describe the state of the art to which this invention pertains.

TECHNICAL FIELD

The present invention relates to the use of an albumin-based colloid composition, such as PEG-Alb, a polyethylene oxide (such as polyethylene glycol (PEG)) modified albumin, for treatment of such diverse hypovolemic conditions as shock, sepsis, bleeding and surgery.

BACKGROUND OF THE INVENTION

Massive resources have been expended on the development of potential therapies aimed at reversing the hypovolemic that is common to different manifestations of systemic inflammatory response syndrome (SIRS). Sepsis alone accounts for 750,000 cases per year in the United States, resulting in 200,000 deaths (1). This high mortality results from multi organ dysfunction (MODS), which is associated with organ edema secondary to capillary leak (CL). Patients with significant CL are typically managed by administering resuscitation fluids containing osmolytes (e.g., albumin, starches, or dextrans) in addition to vasopressors and other supportive measures.

Capillary leak, which is present in different conditions such as multiorgan dysfunction (MODS), sepsis, trauma, burn, hemorrhagic shock, post-cardiopulmonary bypass, pancreatitis and systemic capillary syndrome, causes morbidity and mortality among a large number of hospital patients. Capillary leak (CL) is a central component of MODS, secondary to severe sepsis and systemic inflammatory response syndrome (SIRS). It is characterized by increased capillary permeability resulting in interstitial edema and decreased tissue perfusion leading ultimately to organ failure and death. The leak aspect of capillary leak syndrome (CLS) is reflected in both the release of water into the interstitial space and high molecular weight components of serum which ordinarily would be retained within the capillaries.

Hypovolemic states often lead to hypoperfusion of vital organs, causing organ dysfunction and ultimately resulting in morbidity and death (2). Hypovolemia can occur either rapidly, as with hemorrhagic shock, or progressively due to an underlying disease, with both types involving a systemic inflammatory process. In hemorrhagic shock, hypovolemia occurs due to a rapid and sudden loss of intravascular volume. Upon resuscitation, an inflammatory process may be triggered in reperfused tissues (ischemic-reperfusion injury) causing endothelial cell (EC) injury and capillary leak (CL) leading to a secondary hypovolemic state. In sepsis and other diseases, systemic inflammation is triggered by the disease and in a similar sequence leads to EC injury, CL, and ultimately hypovolemic shock.

Resuscitation with plasma volume expanders remains a mainstay in treating hypovolemia, but with mixed results. The efficacy and safety of volume expanders, including both colloids (e.g., albumin and starches) and crystalloids, continue to be topics of intense research and controversy (3,4). The unpredictable effectiveness of albumin as a plasma expander may be linked to the severity of the underlying EC injury (5). Specifically, if the endothelial integrity is compromised such that albumin can readily extravasate, the leaking albumin may exacerbate the oncotic gradient favoring CL, as opposed to reversing it.

Though the biological mechanisms that induce CL syndrome are poorly understood, some evidence indicates the involvement of inflammatory cytokines. Fluid replacement with solutions of human albumin is only marginally effective since it does not stop the loss of albumin into the extravascular space. Albumin is important because it is responsible for plasma oncotic pressure as well as for retaining sodium ions in the blood.

Under normal conditions, albumin contributes to about 80% of the total blood colloid osmotic pressure (6) and is ideally sized such that it extravasates at a low physiologic rate (7). In CL patients, 5% to 20% albumin solutions are often administered to increase circulating blood volume and to augment intravascular osmotic properties. This method of retarding CL makes the tenuous assumption that albumin can maintain its normally low extravasation rate during shock. Clinical data, however, show that the efficacy of albumin is inconsistent at best (8,9). Some have even suggested that resuscitation with albumin may increase mortality in critically ill patients (10).

PEGylation has been used extensively (11,12). Modification of interferon beta-1a with polyethylene glycol prolongs its half-life, resulting in higher antiviral activity (13). There have been studies on the use of PEGylated hemoglobin (PEG-Hb) as a substitute for blood (14,15,16). Large amounts of PEG-Hb, constituting up to 80% vascular volume showed that PEG-Hb is effective in maintaining the hemodynamics and oxygen delivery in the rat (17). These studies suggest that PEG-Hb is safe even at very high doses.

Other colloids have been used to treat capillary leak conditions with varying degrees of efficacy. A variety of heterogeneous ($M_r$ weighted average: 125,000-450,000 Da) starch colloids have been proposed or are in use as substitute for albumin (18). While these compounds are less expensive and more readily available than pooled human albumin, use of starch colloids has been restricted to low doses due to safety issues that severely limit their use. In addition, the high $M_r$ (>1,000,000 Da) moieties within the heterogeneous starch colloids can alter blood rheological properties and cause coagulopathy (19). The relatively homogeneous Pentastarch ($M_r$=110,000) has been shown to attenuate lung injury in an aortic occlusion reperfusion injury model (20).

In a recent study, MAP and heart rate (HR) did not change favorably when hetastarch (HES) was given in a septic pre-treatment rat model (21). In contrast, favorable changes in MAP (increased) and HR (decreased) were observed in rats pre-treated with polymerized hemoglobin. This occurred despite the fact that, at the same molar concentrations, the colloid osmotic pressure of HES (27 mm/Hg) was higher than the polymerized hemoglobin (21 mm/Hg). Use of the latter as a routine plasma expander is however controversial and is complicated by potential side effects particularly in relation to the kidneys.

Finally, several studies have suggested that albumin has an endothelial anti-apoptotic effect by mediating regulation of cellular glutathione and nuclear Factor Kappa B activation (22,23,24). This may play a significant role in sepsis induced CL particularly in light of a recent report that linked CL in different systemic inflammatory response manifestations to endothelial cell apoptosis (25).

The available albumin today has a molecular weight of 69,000 with a very short half-life (4-6 hours) which can easily leak to the extravascular space in capillary leak conditions such as severe sepsis, pancreatitis, burn and trauma. This leaking can cause worsening edema and/or compartment syndrome. The use of pentastarch and hexastarch are of limited value since they are not for use in pediatric patients and can cause bleeding. Additionally, only 15 cc/kg can be used in patients. Further, the pentastarch and hexastarch have been shown to cause intractable pruritus (itching) after use and the effect lasted for years. In fact, some studies state that the use of albumin as a replacement or as a volume expander is counterproductive since it increases edema by drawing fluid out of the capillaries.

Therefore, there is a great need for a composition and a method to effectively prevent and/or treat hypbvolemic conditions which does not have the above-described disadvantages.

SUMMARY OF THE INVENTION

One aspect of the present invention relates to a composition comprising an albumin-based colloid composition. In one aspect, the albumin-based colloid composition is modified such that its hydrodynamic radius is sufficiently large to preclude its leaking through the capillaries while retaining its oncotic properties and its ability to bind ligands such as sodium ions, fatty acids, drugs and bilirubin. While a number of proteins have been modified with polyethylene glycol, attached through the ε-amino group of lysine, without loss of biological activity and without significant toxicity, no one has before modified human albumin with a PEGylation product (including polyethylene oxide) at multiple sites on the albumin protein. The present invention contemplates the use of PEGylation products which expand the composition's hydrodynamic ratio to a degree such that, when administered to a patient in danger of, or suffering from a hypovolemic state, the albumin-based colloid composition reverses the hypovolemic condition.

The albumin-based colloid composition of the present invention is especially useful for volume expansion in states of shock such as severe sepsis, shock, pancreatitis, burn and trauma, thereby improving survival rates in those conditions.

The albumin-based colloid composition is also useful as a hyperosmotic agent driving, or causing, ultra filtration in peritoneal dialysis. Still other uses include, for example, use in head trauma, hyperviscosity states, patients with liver cirrhosis following parcenthesis, eukopheresis, nutritional albumin deficiency, mephrotic syndrome, liver failure, severe hypoalbuminemic patients, and severe burn patients.

In one aspect, the present invention comprises a composition of an albumin-based colloid composition having a preferred degree of hydration. The present invention further relates to two methods to product the albumin-based colloid composition by modifying the albumin with polyethylene oxide: one is by using N-hydroxysuccinamide esters and the other is by using cyanuric chloride derivatives. The albumin-based colloid composition of the present invention is safe and has an extended useful half-life. The albumin-based colloid composition can be synthesized using recombinant albumin which decreases its immunogenicity.

The albumin-based colloid composition has a lessened tendency to extravascate because of its larger size, thereby avoiding worsening of the hypovolemic condition such as capillary leak syndrome and clinically, edema and compartment syndrome.

In another aspect, the volume-expanding properties of the albumin-based colloid (or example, albumin with covalently attached polyethylene glycol (PEG-Alb) is a large albumin-based colloid composition which has a greater degree of hydration and a larger hydrodynamic radius. The albumin-based colloid composition is less likely to enter the extra vascular space than normal albumin. Additionally, the albumin-based colloid composition retains the important physiologic functions of albumin, including roles as an osmolyte, as an antioxidant, and as a transporter of less soluble metabolites such as heme and bilirubin; the latter two features are not associated with other crystalloids and colloids.

In one aspect, the present invention relates to a composition comprising a large albumin-based colloid with a preferred degree of hydration. The composition is an albumin-based colloid and, in one embodiment, comprises a polyethylene glycol modified albumin having a hydrodynamic radius sufficiently large to preclude the molecule from leaking through a patient's capillaries. In certain embodiments, the albumin-based colloid composition has a molecular weight of at least about 80 to about 250 KD or greater. The composition can comprise human albumin, bovine serum albumin, lactalbumin, or ovalbumin.

The albumin-based colloid composition has an ability to bind ligands such as sodium ions, fatty acids, bilirubin and therapeutic drugs.

In another aspect, the present invention relates to an in vivo method of preventing or treating hypovolemic conditions comprising administering a therapeutic amount of the large albumin-based colloid composition to a patient in danger of developing such conditions.

In another aspect, the present invention relates to a method for the prevention of mammalian tissue injured or at risk of injury comprising the administration of a therapeutic amount to a mammal of a composition comprising an albumin-based colloid. The composition is incapable of leaking through the mammal's capillaries and is present in an amount of sufficient to protect the tissue from injury. The method is especially useful where the risk of injury is due to hypovolemia, sepsis, shock, burn, trauma, surgery, predisposition to capillary leak, hyperviscosity stress, hypoalbuminemia, and/or anoxia.

Yet another aspect of the present invention relates to a method for forming an albumin-based colloid composition which comprises modifying albumin with polyethylene oxide. The albumin is modified by using N-hydroxysuccinamide esters, or, alternatively, is modified by using cyanuric-chloride derivatives. In certain embodiments, the method includes dissolving albumin in potassium phosphate to form an albumin solution, activating methoxy polyethylene glycol with cyanuric chloride and dissolving in water to form a methoxy polyethylene glycol solution, adding the methoxy polyethylene glycol solution to the albumin solution to form a mixture, stirring the mixture for a suitable time at about room temperature, dialyzing the mixture against a phosphate buffered saline solution at about 4° C. for a suitable time, and collecting polyethylene glycol modified albumin. In certain embodiments, the ratio of a volume of the methyoxy glycol solution to a volume of the albumin solution is in the range of about 1 to about 3.

DESCRIPTION OF THE FIGURES

The patent or application file contains at least one drawing executed in color. Copies of this patent or patent application publication with color drawing(s) will be provided by the Office upon request and payment of the necessary fee.

FIGS. 3A-D show the typical histopathologic changes seen in the different treatment groups.

FIG. 5 (Left) the result are presented as $V_e/V_0$ vs $M_r$;. Upward vertical arrows with numbers correspond to approximate elution positions indicated by arrows.

FIG. 6 shows SELDI Mass spectrometry of PEG-Alb and albumin.

DESCRIPTION OF THE PREFERRED EMBODIMENT

According to the present invention, unlike starches, the albumin-based colloid composition retains the important physiologic functions of albumin, including roles as an osmolyte, as an antioxidant (26), and as a transporter of less soluble metabolites such as heme and bilirubin (27); the latter two features are not associated with other crystalloids and colloids. Protein unfolding studies performed on PEG-Alb indicated that albumin functionality is highly preserved).

According to the present invention, the colloid oncotic properties of the albumin-based colloid composition are superior to those of unmodified albumin with regard to plasma volume expansion during treatment of hypovolemic. The albumin-base colloid composition reduces the likelihood of end organ injury, and hence morbidity and mortality, in critically ill patients. The present invention also relates to a method for the pretreatment of septic patients to prevent or ameliorate ARDS and maintain blood pressure. The albumin-based colloid composition of the present invention, with its larger molecular weight (preferably about 80 KD or greater) and augmented colloid osmotic function, is vastly superior to saline or albumin with regard to improving the physiological and histologic manifestations of endotoxin-induced shock.

Figure 1A:
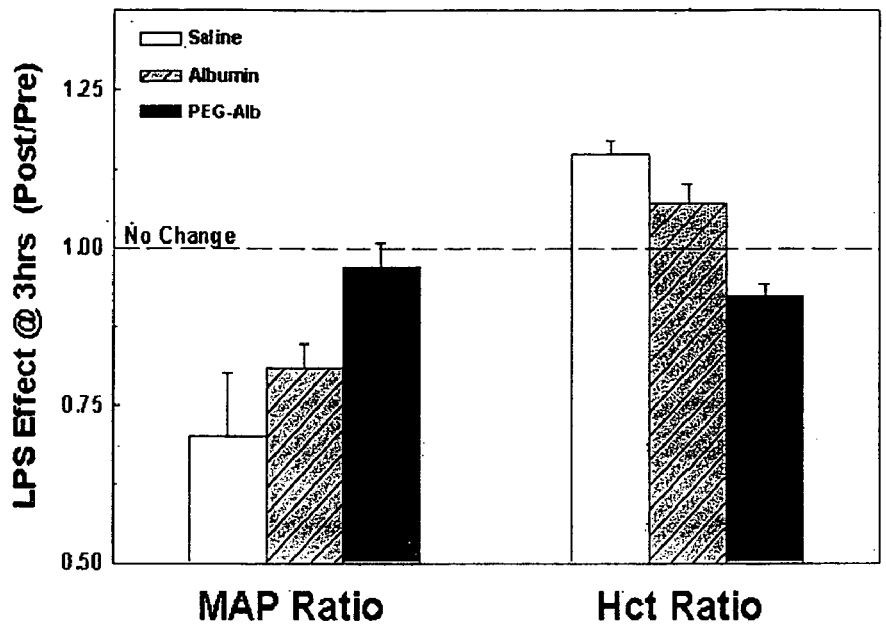
FIG. 1(A). is a graph showing change in hematocrit (%) for the saline, albumin and PEGA groups.

The albumin-based colloid composition is kept in the intravascular compartment in patients, even in sepsis conditions where capillary leak occurs. In the lipopolysaccharide (LPS) induced model of sepsis in rats, there was no difference in hematocrit (HCT) pre-experiment, however after inducing sepsis, the hematocrit of the saline and albumin treated groups increased while that of the PEG-Alb group decreased. FIG. 1 shows the positive difference in the post-pre hematocrit in groups 1 and 2 while there is a negative difference in the post-pre hematocrit of group 3 (PEG-Alb group). The data also shows that albumin tends not to be different with respect to hemoconcentration as well as loss of fluid into the interstitial space.

Figure 2:
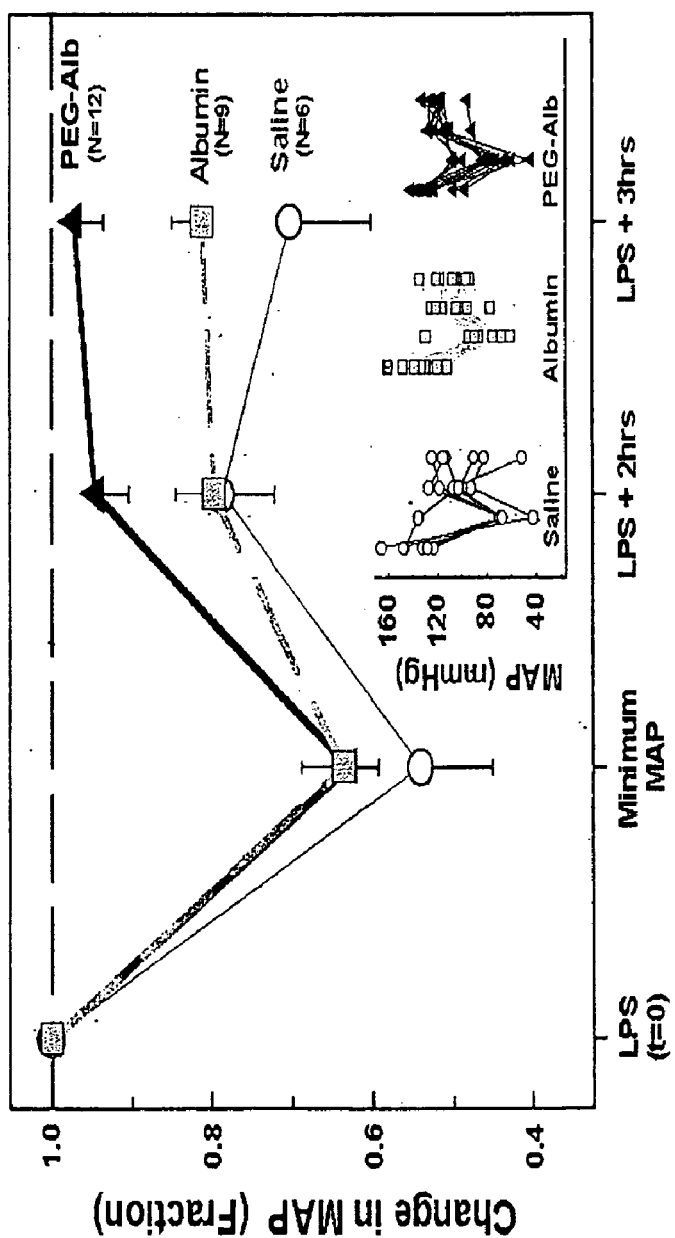
FIG. 2 is a graph showing changes in blood pressure (i.e., mean arterial pressure MAP) (Normalized $P_{art}$) immediately after injection of endotoxin (ET), two hours post injection of ET, and three hours post injection of ET.

The maintenance of blood pressures in sepsis is also important. The efficacy of PEG-Alb, saline and albumin treatments for prevention of sepsis induced hypotension are shown in FIG. 2. At 2 and 3 hours after PLS (lippopolysaccharide), MAP (mean arterial pressure) was decreased compared to baseline values in both albumin and saline treated groups. Alternatively, the average response in PEG-Alb rats was unchanged at both times. Changes in MAP after LPS showed noticeable variability even within treatment groups. Nevertheless, the increased efficacy of PEG-Alb in maintaining MAP was statistically significant (two-way repeated measures ANOVA; P=0.023).

Figure 4:
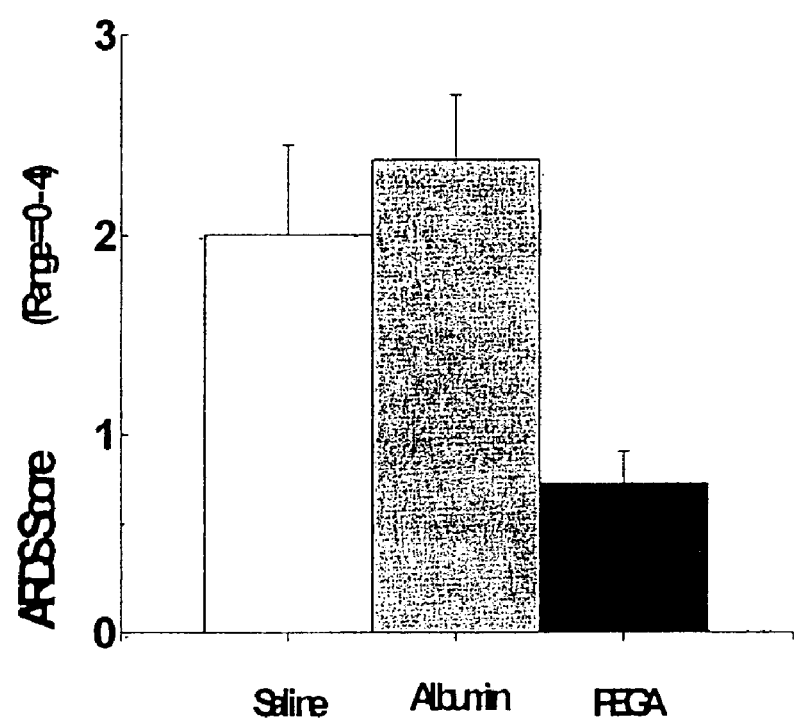
FIG. 4 shows the acute respiratory distress syndrome (ARDS) score of each treatment group.

The histopathologic findings clearly show that the PEG-Alb treated group exhibits less alveolar damage than the albumin group. (FIGS. 3A-D). Lung injury (acute respiratory distress syndrome (ARDS) was significantly less (one-way ANOVA; P-0.002) in PEGA treated rats compared to both albumin and saline treated rats, as shown in FIG. 4. Given the minimal infiltrates and hyalinization in the lung tissues of PEG-Alb rats compared to the positive controls and albumin treated rats, PEG-Alb treatment is better than albumin in LPS-induced hypovolemia.

Figure 5:
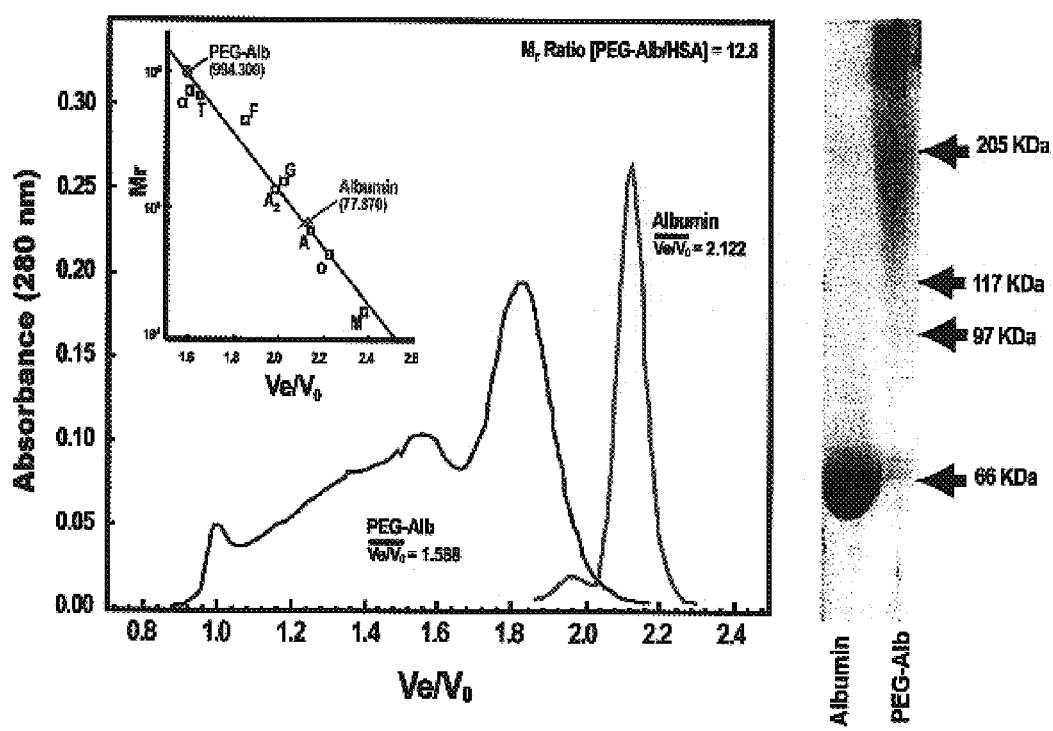
FIG. 5 (Right) shows SDS acrylamide gel electrophoreses showing that estimated MW of PEG-Alb is ≧250,000 daltons. Analytical Gel filtration of PEG-Alb showing samples of albumin, PEG-Alb and standard proteins were chromatographed on Superose 6. The Insert shows vertical arrows with letters indicate the elution position of standard proteins: α, α2 macroglobulin (720,000); thyroglobulin (660,000 $M_r$); F, appoferritin (440,000); $A_2$, albumin dimer (133,000); G, IgG (160,000); O, ovalbumin (45,000); M, myoglobin (17,000).

FIG. 5 (Left ) shows the SDS-Acrylamide gel electrophoresis of PEG-Alb.

Lanes 1 and 4 contain standard markers which are from top to bottom: 1) Myosin (MW 205 KD); 2) Phosphorylase (97 KD); and 3) Bovine serum albumin (66 KD). Lanes 2 contains human serum albumin after pegylation and its molecular weight over 200 KD. Lane 3 contains human serum albumin before pegylation.

FIG. 5 (Right) shows the gel filtration of PEG-Alb on Superdex S200-PEGA size standards was applied to Superdex equilibrated in 10 nM KPO$_4$, 150 nM NaCl. Standards indicated are thyroglobulin (Thyr), immunoglobulin (IgG), albumin (alb), ovalbumin (OVAL) and Myoglobin (My). Peg-albumin eluted as two weeks: Peak I was the void volume and Peak II eluted after thyroglobulin.

According to the present invention, pretreatment of rats with PEG-Alb prior to induction of sepsis with LPS dramatically reduces the manifestations of LPS-induced shock when compared to pretreatment of animals with saline or unmodified albumin. High dose of LPS was given because rodents are relatively resistant to LPS, and sustained hypotension is needed to simulate the severe human sepsis with MODS. PEG-Alb gives a more rapid recovery in blood pressure, a lower hematocrit—suggesting hemodilution as opposed to the hemoconcentration that characterizes CL—and significantly reduced lung injury. The larger effective size of the PEG-Alb molecule renders it less likely to extravasate in the presence of cell injury and during a loss of endothelial integrity.

The shock that follows administration of an endotoxin is characterized by a biphasic blood pressure response. In the first phase, a drop in blood pressure occurs 10-15 minutes after LPS is injected. This was evident in all of the LPS-injected animals, suggesting that PEG-Alb does not act by neutralizing the endotoxin itself. The second phase of hypotension is caused predominantly by the action of inducible nitric oxide(iNOS), which substantially reduces plasma volume (28). It is during this second phase that PEG-Alb has a superior effect when compared with albumin or saline. Although iNOS m RNA or peptide was not measured, it is very likely under these conditions employed here; i.e., intravenous administration of 20 mg/Kg LPS that iNOS was induced. While inherent limitations exist with any pretreatment model, the data show that administering PEG-Alb prior to LPS protects rats from developing ARDS.

The hematocrit, mean arterial pressure, and histology all indicate that PEG-Alb is a beneficial treatment for the LPS-induced hypovolemia. Both the hemodilution and the unchanged MAP achieved with the PEG-Alb treatments are indicative of plasma volume expansion (or at least maintenance), while the opposite effects were observed with both albumin and saline. Maintenance of intravascular volume with PEG-Alb is consistent with reduced capillary leak. Histopathologic findings (FIGS. 3A-D) show minimal interstitial infiltrates and hyalinization in the lung tissues of PEG-Alb-treated rats. Immunflourescence studies show that PEG-Alb tends to be retained in the vascular space to a greater extent than albumin during capillary leak (FIG. 3).

The improved colloidal properties of PEG-Alb result from increased hydrophilic properties, which are shown by its very large hydrodynamic radius-as reflected in its behavior on a gel filtration column and its larger molecular radius of gyration ($R_G$) and excluded volume ($\Lambda$) as inferred from its nonideal osmotic properties. This was also demonstrated using size exclusion chromatography where the elution ratio of PEG-Alb/albumin agreed with the excluded volume of PEG-Alb/albumin (FIG. 5) using colloid osmometry. Similarly increased $R_G$ and $\Lambda$ of proteins after modification with covalent bonding with one or more PEG groups were previously reported in case of bovine hemoglobin by Winslow and colleagues (29).

The colloid oncotic properties of PEG-Alb are superior to those of unmodified albumin with regard to plasma volume expansion during treatment of hypovolemia associated with CL. PEG-Alb is useful to reduce the likelihood of end organ injury, and hence morbidity and mortality, in critically ill patients. The present invention is useful in the pretreatment of patients to prevent or ameliorate ARDS and maintain blood pressure. PEG-Alb, with its larger molecular weight and augmented colloid osmotic function, is vastly superior to saline or albumin with regard to improving the physiological and histologic manifestations of endotoxin-induced shock.

The following examples are provided merely to further illustrate the present invention. The scope of the invention shall not be construed as merely consisting of the following examples.

EXAMPLE I

Use of Polyethylene Glycol Modified Albumin (PEG-Alb) in Sepsis

Materials and Methods: Preparation of PEG-Alb. 2 gms of human albumin (Sigma, St. Louis, Mo.) was dissolved in 45 ml. of 50 MM of potassium phosphate (mixture of mono and dibasic), pH 7.4. 500 mg of methoxy polyethylene glycol (Sigma, St. Louis, Mo.) was activated with cyanuric chloride and dissolved in 4 ml. of water. 1.4 ml of methoxy polyethylene glycol solution was added to 45 ml of the human albumin solution and the mixture was stirred for two hours at room temperature. The mixture was transferred to a dialysing tube (molecular weight cut off—12500) and dialysed against 3000 ml of phosphate buffered saline at 4° C. for 72 hours. The polyethylene gylcol modified albumin (PEGA) was collected and then frozen at −20° C. until its use.

Animals. Adult male Sprague-Dawley rats (Charles River Laboratories, Portage, Mich.) weighing 400-480 grams were used. Animals were housed in an American Association for Accreditation of Laboratory Animal Care, International (AAALACI) approved facility. They were provided standard rat chow and water ad libitum. All protocols were approved by the Institutional Animal Care and Use Committee and the ABC (Hazard) Committee.

Methods:

The animals were fasted overnight, but given water ad libitum. Animals were anesthesized using Sodium pentobaribital (50 mg/kg) intraperitoneally and given additional doses as needed during the course of the experiment. An arterial cathether (Intramedic PE-50, Clay Adams) was placed on the carotid artery and hooked to the transducer/amplifier for continuous blood pressure monitoring (TestPoint, Capital Equipment Corporation, Billerica, Mass.). An intravenous line was placed on the opposite internal jugular vein using G24 cathether. A blood sample was taken from the carotid line for baseline hematocrit and albumin and replacement fluid (1 ml 0.9% saline) was infused via the intravenous line. Normal saline 5 ml was infused in group 1. Albumin 0.6 gms/kg body weight (BW) was given to group 2 and PEGA 0.6 gms/kg BW was given to group 3. After 30 minutes, endotoxin (LPS) (Sigma Chemicals, St. Louis, Mo.) was given to the three groups at varying doses. The rats were divided into 3 groups based on the received resuscitation fluid: Group 1 (n=9) received unmodified albumin in normal saline solution at a 0.6 gm/kg dosage; the injection concentration of albumin was 40 mg/ml, yielding an injection volume of 1.5 ml/100 g body weight (BW). Instead of albumin, Group 2 (n=12) received PEG-Alb at the same dosage, protein concentration, and injection volume as at Group 1. Group 3 (n=6) received 1.5 ml/100 gm BW of normal saline. Blood pressure monitoring was done for three hours after endotoxin infusion after which the rats were euthanized.

Post-experiment blood samples for hematocrit and albumin were taken. The right lung was put in formalin and set to pathology for hematoylin-eosin staining.

PEG-modified albumin (PEG-Alb) was examined as a potential plasma volume expander. Albumin modified at multiple sites, exhibited a larger effective molar volume and exerted greater osmotic pressure than unmodified albumin. Solutions of PEG-Alb, albumin, and saline were tested in a rat endotoxin-induced model of shock. Pretreatment with polyethylene glycol modified-human albumin (PEG-Alb) maintained mean arterial pressure (p=0.023), retained volume as evidenced by hemodilution (p=0.001) and attenuated the histologic manifestations of acute respiratory distress syndrome (ARDS) (p=0.002). Rats were pretreated with fluorescence labeled PEG-Alb and rhodamine labeled albumin, separately and in combination, followed by treatment with LPS. Fluorescence microscopy of lung sections indicated that fluorescence-labeled PEG-Alb was retained within the blood vessels rhodamine-labeled albumin was not. Compared with the use of saline or unmodified human albumin, PEG-Alb is a useful alternative plasma volume expander that may be of use in hypovolemic states.

EXAMPLE II

Use of PEG-Alb to Restore Vascular Volumes and Attenuate Acute Lung Injury in Endotoxin-induced Shock Preparation of albumin and PEGA (PEG-Alb): Methoxy-polyethylene glycol cyanuric chloride (average $M_r$ 5000) was added to human albumin (type V, Sigma Chemical Co.) dissolved in 50 mM $KP_I$ (pH 7.5) at 50 to 60 mg/ml with gentle stirring four times (0.2 mg per mg of albumin per addition) at 10-minute intervals at 22° C. The reaction was allowed to stir 40 minutes after the last addition of the reagent. Modification was rapid, being complete in less than 15 minutes at room temperature with the extent of modification depending primarily on the amount of reagent added. Prior to infusion into animals, both albumin and PEG-Alb were dialyzed against phosphate-buffered saline for 48 hours with three changes of buffer using high-molecular-weight-cutoff dialysis tubing (50 kDa molecular mass cutoff).

FITC-Albumin and FITC-PEG-Alb. Human albumin (50 mg/ml) was incubated 1 hr in 50 mM $KP_I$ (pH 7.5), 150 mM NaCl, and 0.5 mM dithiothreitol. The dithiothreitol-treated albumin was incubated two hours with 4 mM 5-iodoacetamido fluorescein or 1.5 mM tetramethylrhodamine-5-iodoacetamide. The flourescein-modified albumin was dialyzed 48 hours against four changes of phosphate-buffered saline to remove free flourescein. Rhodamine-labeled albumin was chromatographed on Sephadex 50 followed by extensive dialysis against phosphate-buffered saline.

Some of the flourescein-labeled albumin was modified with methoxypolyethylene glycol cyanuric chloride and purified by gel filtration on Sephacryl S200. Fractions from Sephacryl S200 eluting with apparent molecular weights in excess of 200,000 were pooled and concentrated using an Amicon ultrafiltration cell with a PM10 membrane. Analysis of the flourescein and rhodamine-labeled albumins by gel electrophoresis revealed that the fluorescence was associated with the protein; no fluorescence was detected at the positions of free flourescein or rhodamine.

Physiological Studies

Experimental protocols were approved by the Institutional Animal Care and Use Committee (IACUC) and the Academic Chemical Hazardous Committee (ACHC) at the Medical College of Ohio. Adult male Sprague-Dawley rats (Charles River Laboratories, Portage, Mich.) weighing 400-480 grams were used. Animals were housed in an American Association for Accreditation of Laboratory Animal Care, International (AAALACI) approved facility. They were provided standard rat chow and water ad libitum. Prior to the experiment, the animals were fasted overnight, but given water ad libitum.

All rats were anesthetized using sodium pentobarbital (50 mg/kg body weight) intraperitoneally followed with additional intravenous maintenance doses at 1 hour intervals. Mean arterial pressure (MAP) was continuously measured via a catheter (Intramedic PE-50, Clay Adams) placed in the right carotid artery and attached to a blood pressure transducer and amplifier (BLPR and TBM4, World Precision Instruments, Sarasota, Fla.) and collected on a computer (TestPoint, Capital Equipment, Billerica, Mass.). An intravenous line for infusion was inserted in the left jugular vein (G24 Protectiv*Plus, Johnson and Johnson/Ethicon, Arlington, Tex.).

The rats were divided into 3 groups based on the received resuscitation fluid: Group 1 (n=9) received unmodified albumin in normal saline solution at a 0.6 gm/kg dosage; the injection concentration of albumin was 40 mg/ml, yielding an injection volume of 1.5 ml/100 g body weight (BW). Instead of albumin, Group 2 (n=12) received PEG-Alb at the same dosage, protein concentration, and injection volume as at Group 1. Group 3 (n=6) received 1.5 ml/100 gm BW of normal saline. A 1 ml baseline blood sample was taken for baseline hematocrit (Hct) measurement from the carotid line and replaced with the same volume of 0.9% saline. MAP monitoring was initiated at the start of the fluid infusion. After 30 minutes, 20 mg/kg BW of Endotoxin (*E. Coli* lipopoly-saccharide [LPS] from serotype 055:B45, Sigma Chemicals, St. Louis Mo.) dissolved in 1 ml of saline was administered, and the rats were monitored for 3 hours thereafter. A blood sample was then taken for post sepsis Hct assessment, and then rats were euthanized with 150 mg/kg/BW of Pentobarbital IP and exsanguinated. Finally, one kidney and the lungs were harvested and immediately fixed in 10% formalin for subsequent histologic examination.

Histologic Studies

The lung and kidney tissues were removed from formalin solution and subjected to standard processing, including a hematoxylin and eosin stain. These coded preparations were examined with a light microscope by a blinded pathologist, who scored the inflammatory histopathologic features using the following five-point system: 0=no significant histopathologic changes; 1=minimal interstitial inflammatory infiltrates; 2=mild interstitial inflammatory infiltrates with mild hyalinization; 3=moderate interstitial inflammatory infiltrates with moderate hyalinization; 4=severe interstitial inflammatory infiltrates with severe hyalinization. In order to ensure consistency, the same pathologist examined samples on two separate occasions, and the averaged score was used.

Molecular/Biophysical Studies

SDS Gel Electrophoresis. Samples of unmodified albumin and PEGA were prepared for electrophoresis by adding SDS (1%, W/V) and beta mercaptoethanol (5%, V/V) and heating in a boiling water bath for 1 minute. Samples were subjected to electrophoresis on 7.5% or 10% acrylamide gels (30).

Size Exclusion Chromatography. Albumin and PEGA were analyzed by size-exclusion chromatography on a 24 ml bed volume Superose 6 column (Pharmacia). Samples or a mixture of standards (in 0.5 ml) were applied to the column and eluted with 10 mM potassium phosphate (pH 7.5) and 150 mM NaCl at 0.5 ml min$^{-1}$. Absorbance at 280 nm was monitored continuously.

SELDI-TOF Protein Analysis. Surface-enhanced laser desorption/ionization-time of flight (SELDI-TOF) mass spectrometry was used to characterize the PEG-albumin and albumin samples. One microliter of sample (at 1 to 5 mg ml$^{-1}$) was deposited and allowed to air dry directly onto a 2 mm spot of an alaphatically coated aluminum ProteinChip array (H4 ProteinChip, Ciphergen Biosystems, Palo Alto, Calif.). Twice, one half microliter of energy absorbing matrix (EAM, a saturated solution of 3,5-Dimethoxy-4-hydroxycinnamic acid in aqueous 50% acetonitrile and 0.5% triflouroacetic acid) was applied to the sample and allowed to air dry.

The ProteinChip array was transferred to a ProteinChip reader and a laser (N2 320 nm-UV) was focused on the sample in a vacuum chamber. After 2 warming laser shots, proteins absorbed to the matrix were ionized and desorbed from the array surface. Ionized proteins were detected and molecular masses were determined using TOF analysis. The TOF mass spectra were collected in the positive ion mode with a ProteinChip System (PBSII series, Ciphergen) using Ciphergen Peaks (version 2.1b) software. Real-time signal averages of 65 laser shots were averaged to generate each spectrum.

Colloid Osmotic Pressure (COP). Both PEGA-Alb and albumin were prepared for COP measurements in similar fashion. Briefly, samples were dissolved in 10 mM potassium phosphate (pH 7.5), 150 mM NaCl at 50 mg ml$^{-1}$, treated with dithiothreitol (0.5 mM dithiothreitol) for 1 hour at 30° C., and then incubated with iodoacetamide (5 mM iodoacetamide) for 1 hour at 30° C. The acetamidated albumin (5 ml at 50 mg ml$^{-1}$) was then subjected to chromatography on Sephacryl S300 (2.8 cm×40 cm) equilibrated in 10 mM potassium phosphate (pH 7.5) and 150 mM NaCl to reduce albumin dimer and other low and high molecular weight contaminants that otherwise interfere with determination of osmotic pressure. Finally, both albumin and PEGA were dialyzed against several changes of 0.9% NaCl.

COP measurements with each colloid were repeated over a wide range of concentrations using the Wescor Model 4420 colloid osmometer (Logan, Utah). The instrument was blanked with 0.9% saline and calibrated with a 20.2 mOsm albumin standard solution. Note, the concentration of unmodified albumin was determined from absorbance at 280 nm ($\epsilon_{280nm,1\%}$=5.31) (31) and were confirmed by dry weight measurements. PEG-Alb concentrations were estimated from dry weight determination.

COP [π] in terms of concentration [c] were analyzed via a nonlinear least squares fit of the equation to estimate 1) estimate the weighted molecular Mass [Mr] reflected from the ideal component of the π-c relation (32) and 2) the non-ideal contributions of all other virial coefficients via the two parameters B and α:

$$\pi = RT(C/Mr + BC^{\alpha})$$

This form of the equation is a slight modification yet more flexible form of the traditionally employed equation [π=RT (c/Mr+Bc$^2$+Cc$^3$ . . . )] that avoids a priori assumptions of number of virial coefficients; R=63.364 mm Hg M$^{-1}$, c is concentration (g per dl), and T is temperature (295° K.).

Statistical Analysis. The difference between pre and post-LPS hematocrits among these three treatment groups was compared by ANOVA, whereas two-way repeated measures of ANOVA were used to compare mean arterial pressure (MAP) before LPS and at multiple time points after LPS. Individual differences between groups were assessed using a Tukey multiple-comparison test. A p<0.05 was used to indicate statistical significance.

Physiological Studies

Vascular volume contraction/expansion following LPS—induced sepsis was inferred from the changes in MAP and Hct. Both of these measures varied significantly for rats pre-treated with PEG-Alb, albumin or saline. Initially, within 15-25 minutes post LPS bolus infusion, all three groups showed a similar drop of ~40% in MAP (Saline: 135±11 down to 81±30 mmHg; Albumin: 134±14 down to 85±20 mmHg; PEG-Alb: 125±12 down to 79±19 mmHg) (FIG. 2). The MAP recovery that followed was significantly better in PEG-Alb [MAP [3 hrs after LPS]=120±10 mmHg; p=0.023) treated rats compared to both saline (99±29 mmHg) and albumin (108±14 mmHg) treatments. MAP recovery was slightly greater in albumin versus saline treated rats, but this difference was not significant.

Figure 1B:
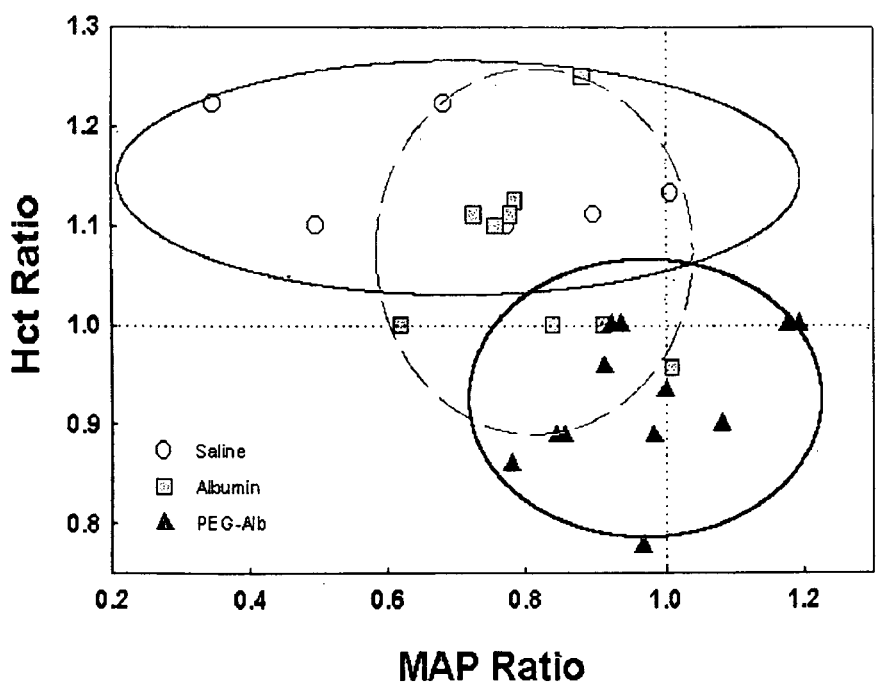
FIG. 1(B). Correlation of mean arterial pressure with hematocrit.

Pre-LPS hematocrit was similar in all study groups [44±2 (saline), 42±3(albumin) and 45±2(PEG-Alb)]. At 3 hours after LPS, hematocrit (post) was elevated relative to baseline (pre) levels for both the albumin (Hct Ratio (post/pre) =1.09±0.11) and saline (Hct Ratio=1.19±0.09) treated rats indicating a relative decrease in intravascular fluid volume or hemoconcentration (FIG. 1-A). Conversely, PEG-Alb-treated rats exhibited hemodilution after LPS administration (Hct Ratio=0.93±0.07). These trends were highly reproducible within each group, and the differences between treatment groups were highly statistically significant (one-way ANOVA; p=0.001). Most importantly, these changes in HCT were generally correlated to the extent of MAP recovery as evidenced by the clustering of the MAP Ratio vs. Hct Ratio(33). Here, PEG-Alb rats generally exhibited Hct Ratios<1 (i.e., hemodilution) and MAP Ratios at or near 1 (i.e., near complete recovery at 3 hours post-LPS). Alternatively, for saline and albumin treated rats, the post-to-pre MAP Ratios were relatively lower (incomplete MAP recovery) while Hct Ratios were generally>1 (hemoconcentration). FIG. 1(B).

Histologic Studies

Microscopic examination of lung tissue sections taken from PEG-Alb-treated and control (no-sepsis) rats did not reveal significant histopathological changes (FIG. 3.A-D). Alternatively, substantial inflammatory histopathologic changes consistent with severe acute lung injury (ALI), including hyalinization and interstitial lymphocytic infiltrates, were evident in most saline and albumin treated rats (FIG. 3). Overall, the averaged ALI scores (0=No injury; 1=minimal; 2=mild; 3=moderate; 4=severe) were significantly lower in PEG-Alb-treated rats (0.76±0.47; range: 0-1) compared to both the saline (2.0±1.0; range: 0-3) and albumin (2.4±0.9; range: 1-4) groups (One Way ANOVA; P=0.002). In all four groups, microscopic sections of the kidneys showed no significant histopathologic changes.

Results from example normal (FIG. 8.A) and septic (FIG. 8.B) rats infused with a mixture of fluorescein-labeled PEG-Alb (green) and rhodamine-labeled albumin (red) exhibited distinctly different distribution patterns of the two chromofores. Specifically, the alveolar—capillary area of the normal rats was characterized by localized yellow (i.e., red and green) compared to more diffuse distribution of the chlorofores in septic rats particularly the red rhodamine suggesting its extravasation. A consistent finding is also evident from septic rats injected with a single colloid species; i.e., either fluorescein-labeled PEG-Alb (FIG. 8.C) and fluorescein-labeled albumin (FIG. 8.D). Here too, the Albumin treated septic rats exhibited diffuse fluorescence while PEG-Alb treated rats did not.

Biophysical Properties of PEG-Alb

Figure 7:
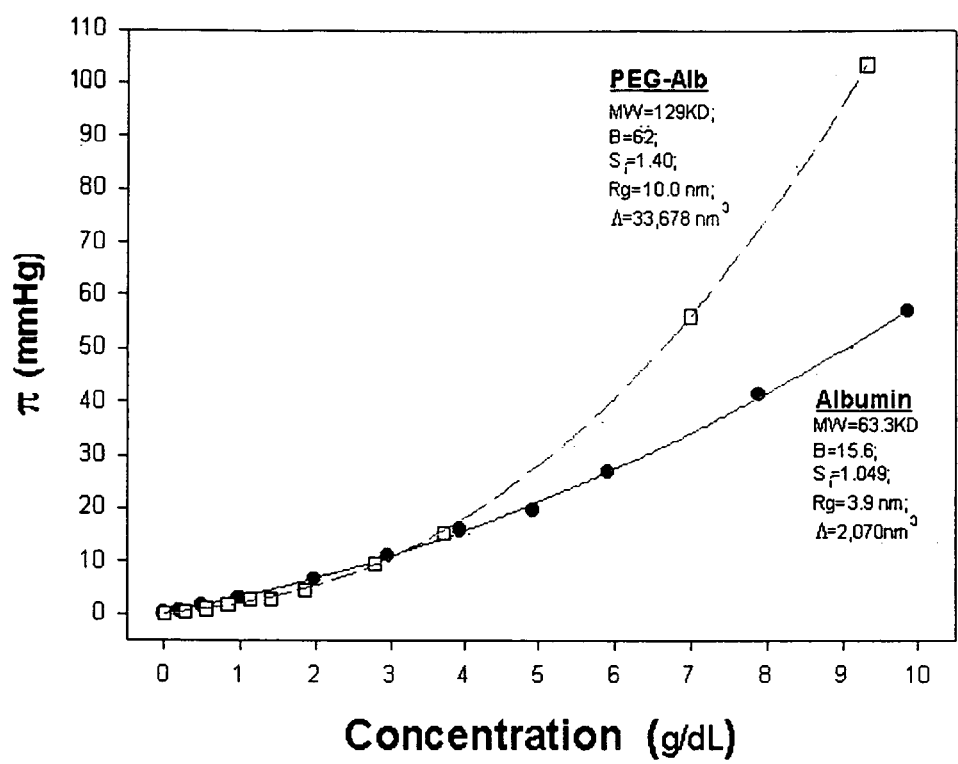
FIG. 7 shows osmotic pressure of PEG-Alb and albumin solutions. The osmotic pressure of solutions of albumin and PEG-Alb were determined as described below and plotted as osmotic pressure (in mm Hg) versus concentration. The line corresponds to a fit to a third order polynomial.
Figure 8A:
FIGS. 8A-E shows fluorescent pictures showing: A and B, normal animals, no sepsis, there is localized Fl-labeled PEG-Alb within the alveolo-capillary membrane, while B, shows an overlap of the Rh-labeled Albumin and Fl-labeled PEG-Alb appearing yellow (green&red). While in animals with sepsis (C, D,E), there is a diffuse distribution of the Rh-labeled albumin and there is a pattern of concentration of the PEG-Alb at the alveob-capillary membrane.
Figure 8B:
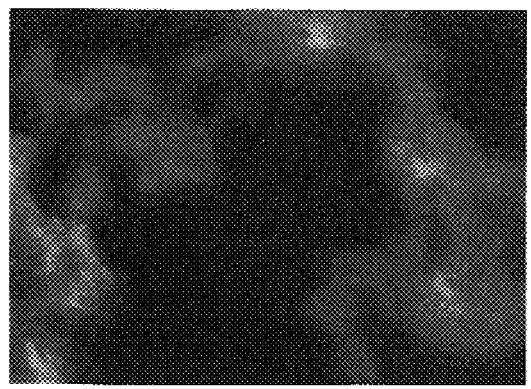
Figure 8C:
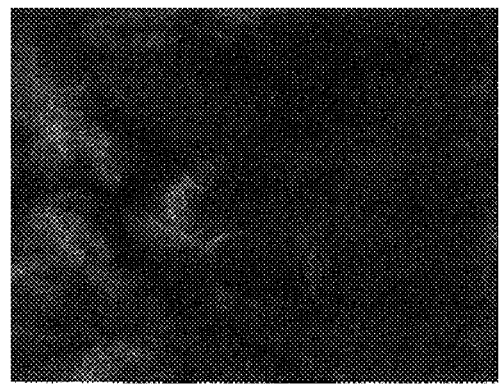
Figure 8D:
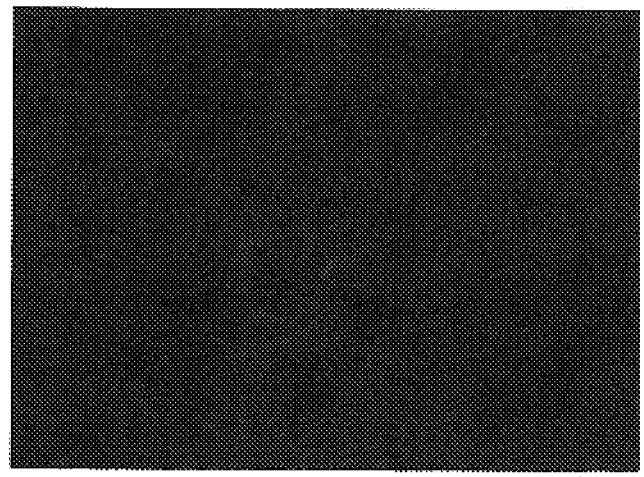
Figure 8E:

Molecular size—The results of SDS gel electrophoresis of albumin and PEG-Alb are contrasted in FIG. 5A (Right). Expectedly, albumin runs as a fairly homogeneous protein and at its known molecular weight. In contrast, while PEG-Alb ran at higher apparent molecular weights, the PEG-Alb material does not readily enter the gel. Note, in case of non-ideal proteins, the electrophoretic mobility is primarily a reflection of their extended nature rather than their molecular weight. The substantial heterogeneity of the modified protein is due to PEG modification at multiple lysyl residues. PEG-Alb was also examined by gel filtration. Consistent with its behavior on SDS gel electrophoresis, the modified protein is substantially heterogeneous, eluting from the column over an apparent $M_r$ range from 500,000 to several million FIG. 5B (Left). Its behavior on a size-exclusion chromatography (SEC) column is also a manifestation of the extended nature of attached PEG, not actual molecular weight. Using the Absorbance—$V_e/V_0$ data for both albumin and PEG-Alb in FIG. 7, we calculated the corresponding mean $V_e/V_0$ to be 2.112 and 1.588, respectively. Effective molecular weights (or size) for the albumin and PEG-Alb in the samples were determined to be about 77,670 Da and 994,300 Da, respectively, or a relative size ratio of about 12.8. The albumin estimate was greater than the known albumin size (67,000 Da) falling between its monomer and dimer weights, and this is consistent with the presence of a two Albumin absorbance peaks—a dominant monomer peak and a smaller dimer peak.

Figures 6A, 6B:
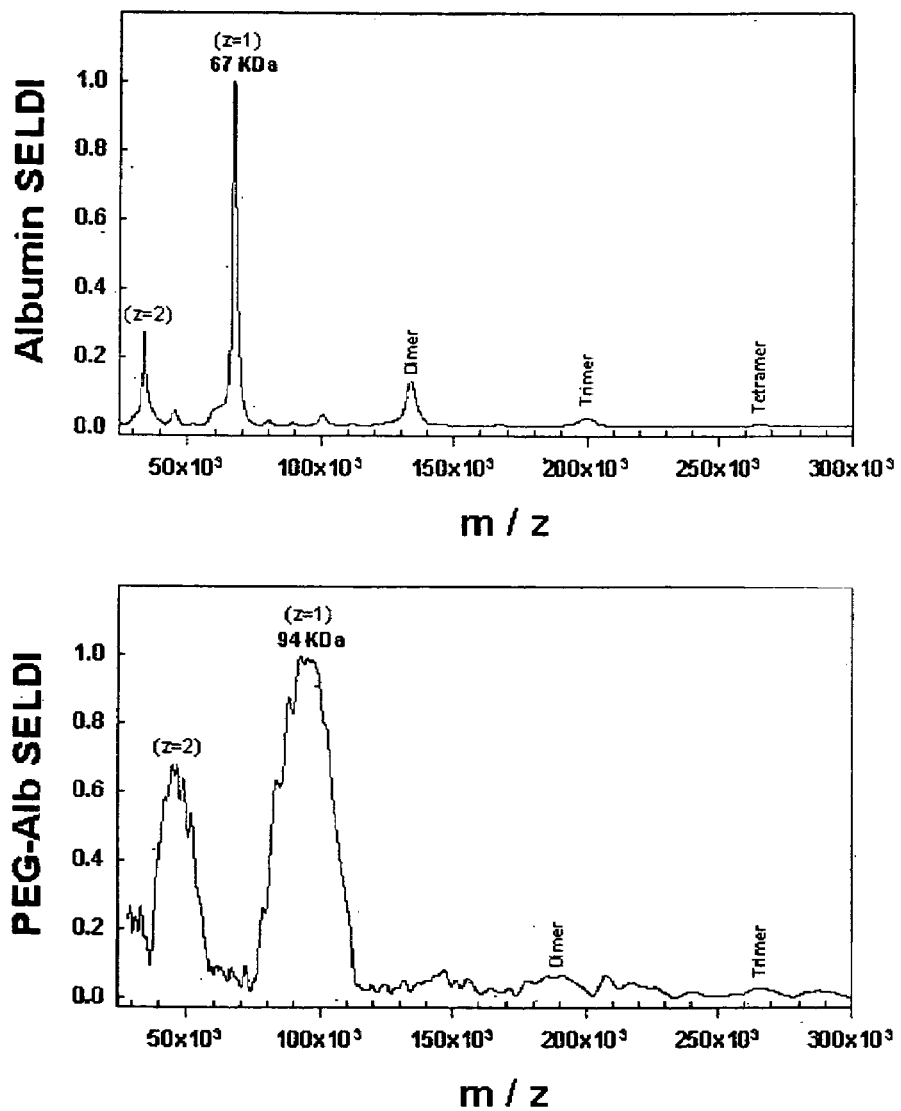
FIG. 6A shows the analysis of 16 pmoles of human albumin.
FIG. 6B shows the analysis of 15 pmoles of PEG-Alb.

To examine the extent of PEG modification by a different technique, albumin and PEGA were analyzed by SELDI-TOF mass spectrometry. Both spectra showed multiple peaks that resulted from the a) presence of monomers and multimers and, more relevantly, b) the detection of singly charged ($z=1$) as well as multi-charged ($z \geq 2$) species. Accounting for these effects, the dominant single-charged albumin monomer spectral peak was centered around a molecular mass of 66,880±2,800 Da.(FIG. 6-A). In contrast, the corresponding PEG-Alb peak was more heterogeneous and exhibited multiple molecular mass species ranging from 77.4 to in excess of 100 kDa separated. These varying PEG-Alb components reflected the number of PEG groups attached by modifying lysyl residues per albumin molecule. Indeed, the mass separation of these PEG-Alb species was consistent with the size of the reagent (5000 $M_r$ average). The mean molecular mass of the PEG-Alb monomer predicted from SELDI-TOF was 94.000 Da±8.000 Da. This corresponded to an average of five to six PEG group attachments per albumin.

Colloid osmotic pressure ($\pi$). To evaluate the properties of PEG-Alb as an osmolyte compared to albumin, we examined their osmotic pressure ($\pi$) over a wide range of concentrations (g/dL). Both albumin and PEG-Alb, albeit differently, showed nonlinear dependence of osmotic pressure with respect to protein concentration (FIG. 7) reflecting their colligative properties, the Donnan effect, and effects arising from their molecular excluded volumes ($\Lambda$). A fit of these $\pi$-concentration data for albumin gave a value of 63,300 for the number-averaged molecular weight, a value of 15.6 for the virial coefficient B, and an $\alpha=2.0^*$. From these coefficients, the computed molecular radius of gyration (Rg) and $\Lambda$ for albumin were 3.9 nm and 2,070 nm$^3$, respectively. All these estimates are in good agreement to previously published values (34). The $\pi$-concentration data for the PEG-Alb showed greater non-ideality or increased curvature compared to albumin. The corresponding number-averaged molecular weight of PEG-Alb was 128,000 Da, B=62, $\alpha=2.40$, Rg=10.0 and $\Lambda=33,378$ nm$^3$. The latter corresponded to a 16-fold relative increase of A after modification with PEG. This relative change in the extended nature of the protein with pegylation is comparable to the 13-fold increase inferred from the SEC measurements on the same proteins.

The two methods for estimating molecular weight (SELDI and colloid osmometry) provided similar estimates for albumin but not PEG-Alb. For the latter, the $\pi$-based estimate was greater than expected at 128,000 Da. Since the osmotic pressure derivation provides a number averaged molecular for all species in the solution, then an overestimate of molecular weight by this method is consistent with the presence of multimers. While not wishing to be bound by theory, it is believed this is a likely explanation of these apparent differences since the SELDI data does indeed suggest the presence of PEG-Alb multimers (FIG. 6).

Compared to saline and albumin, pre-treatment of rats with PEG-Alb prior to LPS-induced septic shock resulted in: 1) a more complete recovery in blood pressure, 2) unchanged or slightly lowered hematocrit, suggesting hemodilution as opposed to hemoconcentration that usually characterizes CL, and 3) significantly reduced lung injury.

Since rodents are fairly resistant, a relatively high dose of LPS was used in the experiments to ensure significant and sustained hypotension as a way of simulating severe human sepsis with MODS (35). The hypotension that follows LPS is characterized by a biphasic response. In the first phase, a sharp rapid drop in arterial pressure occurs within 15-25 minutes of LPS bolus infusion. This phase did not differ among the treatment groups indicating that albumin and PEG-Alb did not alter the initial effects of endotoxin relative to saline. The second phase of hypotension is caused predominantly by the action of inducible nitric oxide (iNOS), which substantially reduces plasma volume via CL (36). While iNOS mRNA or peptide was not measured, it is highly likely that iNOS was induced by the administration of a high LPS dose (20 mg/Kg) (37).

The superior effects of PEG-Alb compared to albumin or saline were manifested in this second hypotension phase of endotoxin shock. Evidence of this included the more complete blood pressure recovery and relative hemodilution. Also, minimal interstitial infiltrates and hyalinization in the lung tissues of PEG-Alb-treated rats were evident from lung histopathology while immunflourescence studies in lung tissues showed greater retention of PEG-Alb intravascularly compared to apparent albumin extravasation in the presence of CL. All these are consistent with less capillary leak and greater plasma expanding properties.

The in vitro measurements show that the substantially larger effective size and greater colloid osmotic pressures of the PEG-Alb molecule, relative to albumin renders, is less likely to extravasate in the presence of cell injury and loss of endothelial integrity. Indeed, SEC and colloid osmometry indicated a 13-16 fold increase in the extended molecular structure/excluded volume after pegylation. The improved colloidal properties of PEG-Alb resulted from increased hydrophilic properties, which are reflected by the larger hydrodynamic/gyration radius ($R_G$) and excluded volumes ($\Lambda$). In a canine model of endotoxic shock, the severity of capillary permeability was inferred by the measurment of different proteins molecular weights by electrophoresis (38). The larger molecular weights corresponded to MW of 900, 000 Da and the smallest being the albumin (60,000 Da). The albumin corresponded to a radius of gyration 3.4 nm and Apopferritin dimer, the largest protein to 12.1 nm, knowing that the larger gaps are far less represented at the endothelium compared to the medium gaps (60,000-500,000 Da) (39), PEG-Alb with its 10. nm size should be retained in the vascular space in moderate to severe leak.

EXAMPLE III

The Synthesis and Purification of Maleimide-PEG Derivatives of Human Albumin were Completed Human albumin (Sigma Chemical Co. type V) at 50 mg ml-1 in 10 mM potassium phosphate (pH 7.5), 150 mM NaCl, and 0.5 mM dithiothreitol was incubated for 1 hour at 30° C. Maleimide-methoxypolyethylene glycol 20,000 Mr (Shearwater Inc. cat. Number 2D2MOP01) or maleimide-methoxypolyethylene glycol 40,000 Mr (Shearwater Inc. cat number 2D2MOP01) was added to 1 mM and the reactions were incubated for 1 hour at 30° C. PEG-modified albumins were purified by ion exchange chromatography on Q-Sepharose )Pharmacia).

Figure 9:
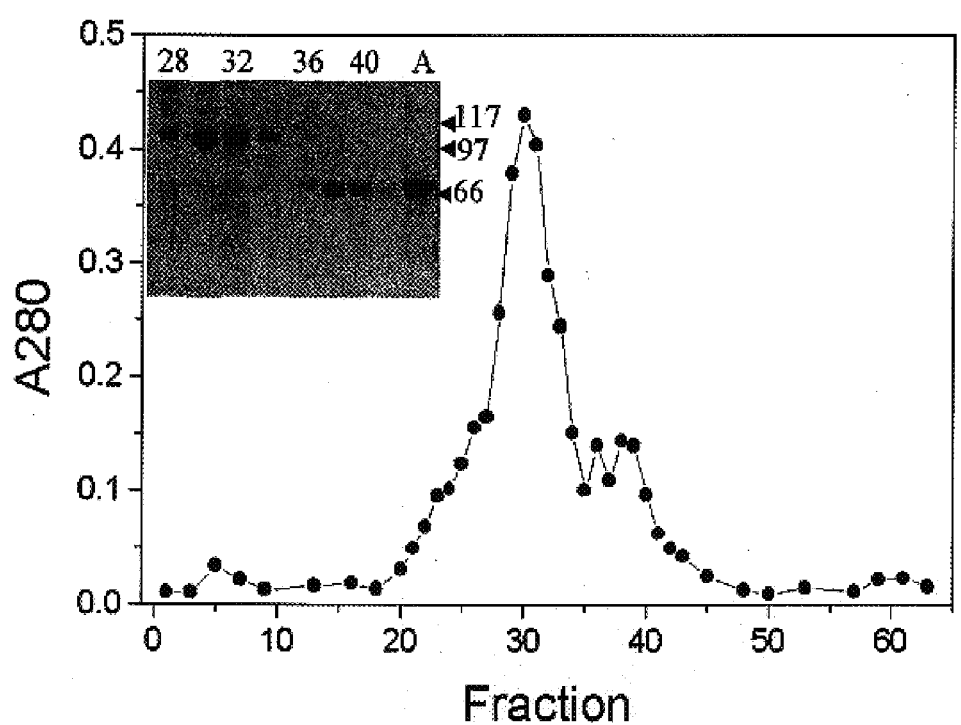
FIG. 9 shows the purification of PEG-20,000 (maleimide) modified albumin—Human albumin modified with maleimide PEG 20,000 (7 mg of protein) was applied to Q-Sepharose (1.5 cm×5 cm) equilibrated in 50 mM Tris-Cl (pH 7.5 at 25° C.).

FIG. 9 shows the purification of PEG-20,000 (maleimide) modified albumin—Human albumin modified with maleimide PEG 20,000 (7 mg of protein) was applied to Q-Sepharose (1.5 cm×5 cm) equilibrated in 50 mM Tris-Cl (pH 7.5 at 25° C.). The column was eluted at 27 ml/hr and fractions of 1.5 ml were collected. Chromatography was performed at room temperature (22° C.). The column was eluted with a gradient of NaCl from 0 to 0.5 M (100 ml total volume) starting at fraction 7. Unmodified albumin elutes between fractions 35 and 43. The inset in the figure shows the results of SDS gel electrophoresis (10% acrylamide gel) on alternate fractions starting with 28. The lane labeled A in the gel inset indicates unmodified albumin run as a marker and the position of molecular weight markers are indicated at the right of the gel.

Figure 10:
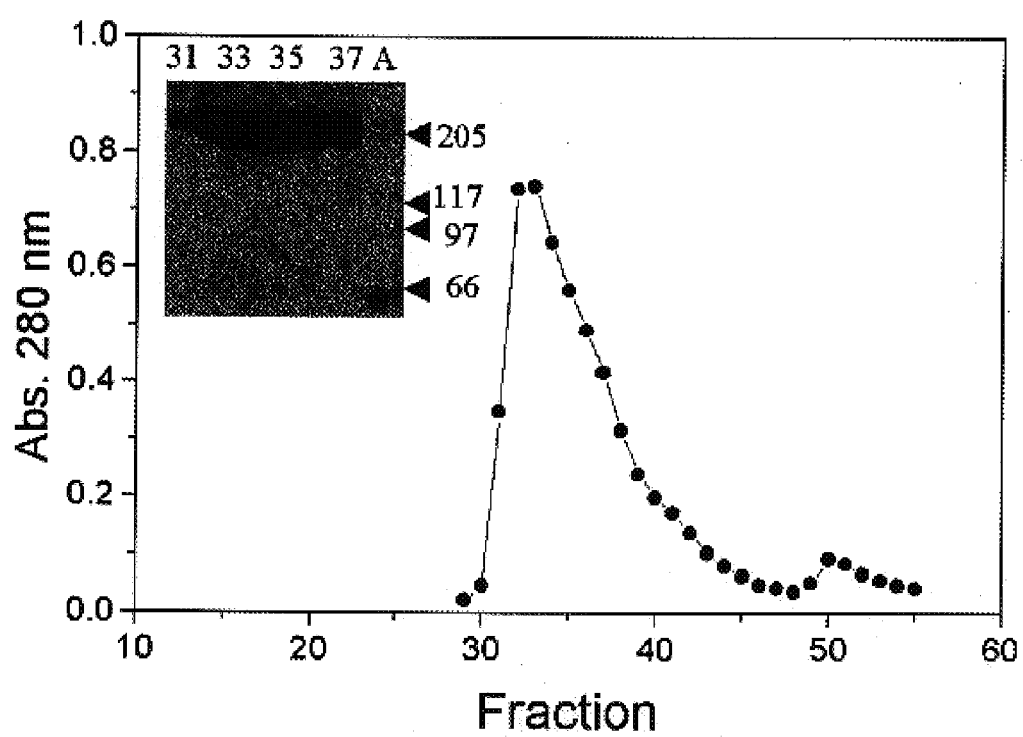
FIG. 10 shows the purification of PEG-40,000 (maleimide) modified albumin—Human albumin modified with maleimide PEG 40,000 (60 mg of protein) was applied to Q-Sepharose (1.5 cm×15 cm) equilibrated in 50 mM Tris-Cl (pH 7.5 at 25° C.

FIG. 10 shows the purification of PEG-40,000 (maleimide) modified albumin—Human albumin modified with maleimide PEG 40,000 (60 mg of protein) was applied to Q-Sepharose (1.5 cm×15 cm) equilibrated in 50 mM Tris-Cl (pH 7.5 at 25° C.). Chromatography was performed at room temperature (22° C.). The column was eluted at 27 ml/hr and fractions of 4 ml were collected. The column was eluted with a linear gradient of NaCl (250 ml total volume) from 0 to 0.3 M starting at fraction 15. Unmodified albumin elutes between fractions 45 and 55. The inset in the figure shows the results of SDS gel electrophoresis (10% acrylamide gel) on successive fractions starting with 31. The lane labeled A in the gel inset indicates unmodified albumin run as a marker and the position of molecular weight markers are indicated at the right of the gel.

While this invention has been described with emphasis upon preferred embodiments, it would be obvious to those of ordinary skill in the art that preferred embodiments may be varied. It is intended that the invention may be practiced otherwise than as specifically described herein. Accordingly, this invention includes all modifications and claims spirit and scope of the appended claims.

REFERENCES

1. Angus, D. C. Wax, R. S. 2001 Epidemiology Of Sepsis-An Update. Critical Care Medicine. 29 (7) S109-S116,
2. Baue, A. E., Durham, R, Faist, E. 1998 Systemic Inflammatory Response Syndrome(SIRS)Multiple Organ Dysfunction Syndrome(MODS), Multiple Organ Failure (MOF) Are We Winning The Battle?. Shock. 10 (2) 79-89.
3. Roberts, J. S., Bratton, S. L. 1998. Colloid volume expanders: problems, pitfalls and possibilities. Drugs. 55(5): 621-630.
4. Berger, A. 1998. Why albumin may not work (editor's commentary). BMJ. 317: 240.
5. Doweiko, J. P., and Nompleggi, D. J. 1991, Use of albumin as a volume expander, J Parenter. Enteral. Nutr. 15, 212-214.
6. 13. Emerson, T. E. 1989. Unique features of albumin: a brief review. Crit Care Med. 17(7): 690-694.
7. Margarson M. P., Soni. N. 1998. Serum Albumin: touchstone or totem? Anaesthesia, 53:789-803.
8. McClelland. 1998. Human albumin administration in critically ill patients. BMJ. 317: 882-886.
9. Wilkes, M., and Navickis, R. J. 2001. Patient survival after human albumin administration. Ann Intern Med. 135: 149-164
10. Cochrane Injuries Group Albumin Reviewers. 1998. Human albumin administration in critically ill patients: systematic review of randomized controlled trials. BMJ. 317: 235-40.
11. Delgado, C., Francis, G. E. and Fisher, D. 1992. The uses and properties of PEG-linked proteins. Critical Reviews in Therapeutic Drug Carrier Systems. 9(3,4): 249-304.
12. Abuchowski, A., van Es, T., Palozuk, N. C., and Davis, F. 1977, Alteration of immunological properties of bovine serum albumin by covalent attachment of polyethylene glycol. J Biol Chem. 252(11): 3578-3581.
13. Kozlowski A; Charles S A; Harris J M, 2001, Development of pegylated interferons for the treatment of chronic hepatitis C. BioDrugs 15, 419-29
14. Conover, C., Malatesta, P., Lejuene, Chang, C. L., and Shorr, R. G. L. 1996. The effects of hemodilution with polyethylene glycol bovine hemoglobin (Peg-Hb) in a conscious porcine model. J Inves Med. 44(5): 238-246.
15. Conover, C. D., Lejuene, L., Shum, K., Gilbert, C., and Shorr, R. G. 1997. Physiological effect of polyethylene glycol conjugation of stroma-free bovine hemoglobin in the conscious dog after partial exchange transfusion. Artif Organs. 21(5): 369-78.
16. Conover, C. D., Linberg, R., Lejuene, L., Nagy, M., and Shum, K. L. 1999. PEG-hemoglobin as a resuscitation solution in the treatment of hypovolemic shock in the anesthetized rat. Artif Organs. 23(12): 1088-1098.
17. Yeh, T., Parmar, J. M., Rebeyka, I. M., Lofland, G. K., Allen, E. L., Dignan, R. J., et al. 1992. Limiting edema in neonatal cardiopulmonary bypass with narrow-range molecular weight hydroxyethyl starch. J Thorac Cardiovasc Surg. 104: 659-65.
18. Axon, R. N. Baird, M. S. Lang, J. D. Brix, A. E. Nielson V G. 1998. Pentalyte Decreases Lung Injury After Aortic Occlusion-Reperfusion. Am J Reespir. CritCare Med. 157-1982-1990
19. Heneka M. T., Loschmann, P. A, Osswald H. 1997. Polymerized Hemoglobin Restores Cardiovascular and Kidney Function in Endotoxin -induced Shock in the Rat. J. Clin. Invest. 99;47-54.
20. Zoellner, H., Hofler, M., Beckmann, R., Hufnagl, Vanyek, E., Blelek E, et al. 1996. Serum albumin is a specific inhibitor of apoptosis in human endothelial cells. J Cell Science. 109: 2571-2580.
21. Cantin, A. M., Paquette, B., Richter, M., and Larivee, P. 2000. Albumin-mediated regulation of cellular glutathione and nuclear factor Kappa B activation. Am J Respir Crit Care Med, 162: 1539-1546.

22. Assaly, R, Olson, D, Hammersely, J, Fan, P S, Liu J, Shapiro J, Kahaleh, B. 2001. Initial Evidence of Endothelial Cell Apoptosis as a Mechanism of Systemic Capillary Leak Syndrome. Chest: 120:1301-1308.
23. Quinlan, G. J., Margarson, M. P., Mumby, S., Evans, T. W., Gutteridge, J. M. C. 1998. Administration of albumin to patients with sepsis syndrome: a possible beneficial role in plasma thiol repletion. *Clin Sci*. 95: 459-465.
24. Filep, J. G., Delalandre, A., Beauchamp, M. 1997. Dual role for nitric oxide in the regulation of plasma volume and albumin escape during endotoxin shock in conscious rats. *Circ Res*. 81: 840-847. problems and solutions. Biomaterials 22,405-417.
25. 12. Vandegriff, K. D., McCarthy, M., Rohlfs, R. J., and Winslow, R. M. (1997) Colloid osmotic properties of modified hemoglobins: chemically cross-linked versus polyethylene glycol surface-conjugated. Biophys. Chem. 69, 23-30.
26. Laemmli, U. K. 1970. Cleavage of structural proteins during the assembly of the head of bacteriophage T4. *Nature*. 227:6980-6985.
27. Peters, T. 1996, All About Albumin, Academic Press,
28. Tanford, C., 1961, Physical Chemistry of Macromolecules, John Wiley and Sons, New York, p 217.
29. Johnson, D. E. 1998, Applied Multivariate Methods for Data Analysis. Duxbury Press. Page 319-121.
30. Bullock, J., 1996, Characterization of Polyethelene glycol-Modified Superoxide Dismutase: Comparison of Capillary Electrophoresis and Marix-Assisted Laser Desorption/Ionization Mass Spectometry. Anal. Chem. 68,3258-3264.
31. Veronese F. M. 2001. Peptide and protein PEGylation: a review of problems and solutions. Biomaterials. 22.405-417.
32. Nathan, C. 1997. Inducibile Nitric Oxide Synthase: What Difference Does It Make? J. Clin. Invest. 100(10): 2417-2423.
33. Hubbard, J. D., Janssen, H. F. 1988. Increased microvascular permeability in canine endotoxic shock: protective effects of ibuprofen. *Circ Shock*. 26: 169-183.
34. Taylor, A E, Granger D N,: 1984. Exchange of macromolecules across the microcirculation. Handbook of Physiology. The Cardiovascular System IV, Am Physiol Soc, 4(1):11,467-520.

We claim:

1. An in vivo method of treating a patient suffering from a hypovolemic condition comprising administering a therapeutic amount of a polyethylene glycol-albumin colloid composition to said patient, wherein the polyethylene glycol-albumin colloid composition reduces the risk of organ injury and treats hypovolemic conditions by restoring vascular volumes.

2. The method of claim 1, wherein the polyethylene glycol used in the polyethylene glycol-albumin colloid composition has a molecular weight of 5,000 or greater based on SDS-PAGE.

3. The method of claim 1, wherein the polyethylene glycol-albumin colloid composition has a molecular excluded volume and a hydrodynamic radius sufficiently large to preclude the composition from leaking through a patient's capillaries.

4. The method of claim 1, where the hypovolemic condition is due to sepsis, shock, burn, trauma, surgery, predisposition to capillary leak, hyperviscosity states, hypoalbuminemia, leukopheresis, nutritional albumin deficiency, nephritic syndrome, liver failure, and/or anorexia.

5. The method of claim 1, wherein the polyethylene glycol-albumin-colloid compositon has a molecular excluded volume and the molecular excluded volume of the colloid composition is 16 fold larger than the molecular excluded volume of the albumin.

6. The method of claim 1, wherein the polyethylene glycol-albumin-colloid composition has a hydrodynamic radius and the hydrodynamic radius of the colloid composition is 13 fold larger than the hydrodynamic radius of the albumin.

7. The method of claim 1 wherein the colloid composition has a hydrodynamic/gyration radius ($R_G$) of 10 nm.

* * * * *